United States Patent
Koch et al.

(10) Patent No.: US 6,787,677 B2
(45) Date of Patent: Sep. 7, 2004

(54) HYDROGENATION OF CARBONYL COMPOUNDS

(75) Inventors: Michael Koch, Speyer (DE); Steffen Maas, Bubenheim (DE); Wolfgang Jürgen Pöpel, Darmstadt (DE); Matthias Dernbach, Dossenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/473,213

(22) PCT Filed: Apr. 17, 2002

(86) PCT No.: PCT/EP02/04250

§ 371 (c)(1),
(2), (4) Date: Sep. 29, 2003

(87) PCT Pub. No.: WO02/085825

PCT Pub. Date: Oct. 31, 2002

(65) Prior Publication Data

US 2004/0082821 A1 Apr. 29, 2004

(30) Foreign Application Priority Data

Apr. 21, 2001 (DE) .......................... 101 19 719

(51) Int. Cl.$^7$ .......................... C07C 27/04; C07C 29/14; C07C 31/18; B01J 23/70; B01J 23/00
(52) U.S. Cl. .................. 568/862; 568/852; 568/853; 568/861; 568/863; 568/462; 568/449; 568/458; 502/345; 502/350; 502/346; 502/351; 502/103; 502/113

(58) Field of Search .................. 568/462, 449, 568/458, 852, 853, 861, 862, 863; 502/345, 350, 346, 351, 103, 113

(56) References Cited

U.S. PATENT DOCUMENTS

| 3,923,694 A | 12/1975 | Cornthwaite |
| 4,666,879 A | 5/1987 | Kelly et al. |
| 5,658,843 A | 8/1997 | Tsukada et al. |
| 6,187,957 B1 | 2/2001 | Meyer et al. |
| 6,448,457 B1 | 9/2002 | Hesse et al. |

FOREIGN PATENT DOCUMENTS

| DE | 195 05347 | 9/1995 |
| DE | 198 09418 | 9/1999 |
| DE | 199 63409 | 7/2001 |
| DE | 199 63441 | 7/2001 |
| EP | 301 853 | 2/1989 |

Primary Examiner—Elvis O. Price
(74) Attorney, Agent, or Firm—Keil & Weinkauf

(57) ABSTRACT

In a process for the catalytic hydrogenation of a carbonyl compound or a mixture of two or more carbonyl compounds in the presence of catalyst tablets which comprise an inorganic, $TiO_2$-containing support and, as active component, copper or a mixture of copper with at least one metal selected from the group consisting of zinc, aluminum, cerium, nobel metals and metals of transition group VIII and whose copper surface area is not more than 10 m$^2$/g, the diameter d and/or the height h of the tablets is less than 3 mm.

5 Claims, No Drawings

HYDROGENATION OF CARBONYL COMPOUNDS

The invention relates to a process for the catalytic hydrogenation of carbonyl compounds in the presence of copper-containing catalyst tablets and to the copper-containing catalyst tablets themselves.

The catalytic hydrogenation of carbonyl compounds such as aldehydes for producing simple and functionalized alcohols is acquiring an important position in production streams of the basic chemicals industry. This applies particularly to the hydrogenation of aldehydes which are obtainable via the oxo process or the aldol reaction.

The catalytic hydrogenation of carbonyl compounds is carried out virtually exclusively in fixed-bed reactors in industrial processes. Catalysts used include not only catalysts of the Raney type but also, in particular, supported catalysts, for example copper, nickel or nobel metal catalysts.

U.S. Pat. No. 3,923,694 describes, for example, a catalyst of the copper oxide/zinc oxide/aluminum oxide type. The disadvantage of this catalyst is that it is not sufficiently mechanically stable during the reaction and therefore disintegrates relatively quickly. This results in a loss in activity and a buildup of a differential pressure over the reactor due to the disintegrating catalyst bodies. As a consequence, the plant has to be shut down prematurely.

DE-A 195 05 347 describes in quite general terms a process for producing catalyst tablets having a high mechanical strength, in which a metal powder or a powder of a metal alloy is added to the material to be tabletted. For example, aluminum powder or copper powder is added as metal powder. However, the addition of aluminum powder in the case of a copper oxide/zinc oxide/aluminum oxide catalyst results in a shaped body which has a worse lateral compressive strength than a shaped body which has been produced without addition of aluminum powder, and the shaped body of the invention when used as catalyst displayed a worse conversion activity than catalysts which had been produced without addition of aluminum powder. The document likewise discloses a hydrogenation catalyst comprising NiO, $ZrO_2$, $MoO_3$ and CuO to which Cu powder, inter alia, was added during production. However, this document says nothing about the selectivity or the activity.

DE 198 09 418 describes a process for the catalytic hydrogenation of a carbonyl compound in the presence of a catalyst comprising a support consisting predominantly of titanium dioxide and, as active component, copper or a mixture of copper with at least one metal selected from the group consisting of zinc, aluminum, cerium, nobel metals and metals of transition group VIII, where the copper surface area is not more than 10 $m^2/g$. Preferred support materials are mixtures of titanium dioxide with aluminum oxide or zirconium oxide or aluminum oxide and zirconium oxide. In a preferred embodiment, the catalyst material is shaped with addition of metallic copper powder.

It is an object of the present invention to provide a process for the catalytic hydrogenation of carbonyl compounds using a catalyst which can be produced industrially in a simple manner, has a sufficiently high mechanical stability under the reaction conditions occurring in such a process and, in particular makes it possible to achieve long catalyst operating lives and high conversions and selectivities.

It has been found that tabletting a dried powder comprising the support material, the active component and a customary tabletting aid, e.g. graphite, together with metallic Cu powder to form catalyst tablets having a diameter d and/or a height h of less than 3 mm leads to high activities and selectivities and to good stability of the catalyst.

Accordingly, the abovementioned object is achieved by a process for the catalytic hydrogenation of a carbonyl compound or a mixture of two or more carbonyl compounds in the presence of catalyst tablets which comprise an inorganic, $TiO_2$-containing support and, as active component, copper or a mixture of copper with at least one metal selected from the group consisting of zinc, aluminum, cerium, nobel metals and metals of transition group VIII and whose copper surface area is not more than 10 $m^2/g$, wherein the diameter d and/or the height h of the tablets is less than 3 mm.

As support, preference is given to using $TiO_2$ or a mixture of $TiO_2$ and $Al_2O_3$ or a mixture of $TiO_2$ and $ZrO_2$ or a mixture of $TiO_2$, $Al_2O_3$ and $ZrO_2$, particularly preferably $TiO_2$.

The catalyst used in the process of the present invention is produced by applying the active component copper to the support material used, with there being no restrictions in respect of the application method.

In particular, the following application methods are possible:

a) application of a copper salt solution in one or more impregnation steps to a previously produced inorganic support. The support is dried after the impregnation and calcined if appropriate.

a1) The impregnation can be carried out by the "incipient wetness" method in which the support is treated with an amount of the impregnation solution corresponding to its water absorption capacity so that it is just saturated. However, the impregnation can also be carried out with the support covered by the solution.

a2) In multistage impregnation processes it is advantageous to dry and if appropriate calcine the support between individual impregnation steps. Multistage impregnation is particularly advantageous when the support is to be treated with a relatively large amount of copper.

a3) The inorganic support material is preferably used as a preshaped composition in the impregnation, for example as powder, spheres, extrudates or tablets. Particular preference is given to using powder.

a4) As solvent for the copper salts, preference is given to using concentrated aqueous ammonia.

b) Precipitation of a copper salt solution onto a previously produced, inert inorganic support. In a particularly preferred embodiment, the latter is present as a powder in an aqueous suspension.

b1) In one embodiment (i), a copper salt solution is precipitated, preferably by means of sodium carbonate solution. As initial charge, use is made of an aqueous suspension of the support material.

b2) In a further embodiment (ii), the precipitated catalyst can be produced in a two-stage process. Here, the first step comprises producing and drying a powder as described in a). This powder is converted into an aqueous suspension and used as substrate in a second step equivalent to embodiment (i).

The precipitated solids resulting from a) or b) are filtered off in a customary manner and preferably washed free of alkali.

Both the final products from a) and those from b) are dried at from 50 to 150° C., preferably at 120° C., and subsequently calcined if appropriate, preferably for 2 hours at generally from 200 to 400° C., in particular from 200 to 220° C.

As starting materials for a) and/or b), it is in principle possible to use all Cu(I) and/or Cu(II) salts soluble in the solvents used for the application to the support, for example sulfates, nitrates, chlorides, carbontes, acetates, oxalates or ammonium complexes. For method a), particular preference is given to using copper carbonate, while method b) is particularly preferably carried out using copper nitrate.

To produce the catalyst tablets of the present invention, the above-described dried powder is shaped by means of a suitable tabletting press to form tablets having a diameter d of less than 3 mm and/or a height h of less than 3 mm, preferably d and/or h of less than 2 mm, particularly preferably d and/or h of 1.5 mm. As tabletting aid, graphite is added in the shaping process, preferably in an amount of 3% by weight, based on the weight of the dried powder.

As further additive in addition to the above-described powder and to graphite, metallic Cu powder is added in the production of the catalyst. Preference is given to adding, based on the weight of the above-described dried powder, from 5 to 40% by weight of metallic Cu powder, in particular from 15 to 20% by weight.

The catalyst tablets can be symmetrical, i.e. the height h and the diameter d are identical, or unsymmetrical, i.e. the height h and diameter d are different, but d and/or h are less than 3 mm. In the case of the unsymmetrical tablets, the ratio d:h can be up to 1:2, i.e. the maximum height of the tablets is twice the diameter of the tablets. In the process of the present invention, particular preference is given to using symmetrical catalyst tablets in which the diameter d and the height h are each 1.5 mm.

The present invention therefore also provides a catalyst tablet which comprises an inorganic support comprising $TiO_2$ and, as active component, copper or a mixture of copper with at least one metal selected from the group consisting of zinc, aluminum, cerium, nobel metals and metals of transition group VIII, whose copper surface area is 10 $m^2/g$ and which is obtainable by a process which comprises a tabletting step in which metallic copper powder is added, wherein the diameter d and/or the height h of the tablet is less than 3 mm.

The shaped tablets of the present invention are preferably heat-treated for 2 hours at from 300 to 600° C., in particular from 400 to 500° C. This novel tabletting process allows, compared to the exclusive use of graphite as tabletting aid in the customary processes, the powder to be shaped to form tablets particularly easily and gives very chemically and mechanically stable catalysts.

The surface area of the catalyst tablet is determined by the BET method using $N_2$ adsorption, in particular as specified in DIN 66 131. The mean pore diameter and the pore size distribution are determined by means of Hg porosimetry, in particular as specified in DIN 66 133.

The parameters "hardness" and "abrasion" can be determined as follows. To determine the cutting hardness, specimens are parted by means of a blade. The force which has to be applied to the blade to cut through the specimen is referred to as the cutting hardness of the material.

The fracture hardness (fracture strength) of spherical specimens is determined by placing the sphere under a punch having a defined area and pressing the punch against the sphere until the latter breaks. The pressure which needs to be applied to the specimen by the punch for fracture to occur is referred to as the fracture hardness.

The abrasion is determined by means of a vibratory mill. In this test, catalyst material having a particular particle size range is aggitated together with porcelain balls in a container at a high rotation rate for a particular period of time. The catalyst is then sieved out again. The weight loss in percent is then designated as the abrasion, as is described in chapter 6 of J.-F. Le Page et al., "Applied Heterogeneous Catalysis", Editions Technip, Paris (1987).

The lateral compressive strength is determined for the purposes of the present invention by means of an instrument model "Z 2.5/T 919" from Zwick (Ulm), and the abrasion was determined in accordance with ASTM Designation D 4058-81. The measurements were carried out under a nitrogen atmosphere to avoid reoxidation of the catalysts.

Activation of the ignited catalyst is carried out either before or after installation in the reactor.

If the catalyst is to be used in its reduced form, it is installed in the reactor and supplied directly with the hydrogenation solution under hydrogen pressure. When it is used in the oxidic form, the catalyst is prereduced by means of reducing gases, for example hydrogen, preferably hydrogen/inert gas mixtures, in particular hydrogen/nitrogen mixtures, at from 100 to 300° C., preferably from 150 to 250° C., in particular from 180 to 240° C., before it is supplied with the hydrogenation solution. Preference is given to using a mixture having a hydrogen content of from 1 to 100% by volume for the prereduction.

A characteristic parameter of the catalysts of the present invention is the specific copper surface area. This is calculated from the $N_2O$ consumption determined in the oxidation of surface copper atoms by gaseous $N_2O$ in a heated sample.

For this purpose, the sample is firstly treated with 10 mbar of hydrogen at 240° C. for 10 minutes. The sample is subsequently evacuated to a pressure of less than $10^{-3}$ mbar and is then treated with 30 mbar of $H_2$ for 10 minutes, subsequently evacuated once more to less than $10^{-3}$ mbar, treated with 100 mbar of $H_2$ for 3 hours, evacuated again to less than $10^{-3}$ mbar and finally treated with 200 mbar of $H_2$ for 15 hours, with the treatment with hydrogen being carried out in each case at 240° C.

In a second step, the sample is treated with $N_2O$ at 70° C. and a pressure of 266 mbar for 2 hours, during which decomposition of the $N_2O$ on the sample can be observed. The sample is subsequently evacuated to less than $10^{-3}$ mbar and the increase in the mass of the catalyst as a result of formation of copper oxide on the surface of the catalyst is then determined.

The specific copper surface area measured in this way on the catalysts produced according to the present invention is generally not more than 10 $m^2/g$, preferably from 0.1 to 10 $m^2/g$, more preferably in the range from 0.5 to 7 $m^2/g$, in particular in the range from 0.5 to 5 $m^2/g$.

The present invention therefore also provides a catalyst tablet which comprises an inorganic, $TiO_2$-containing support and, as active component, copper or a mixture of copper with at least one metal selected from the group consisting of zinc, aluminum, cerium, nobel metals and metals of transition group VIII and whose copper surface area is not more than 10 $m^2/g$, wherein the diameter d and/or the height h of the tablet is less than 3 mm.

A preferred field of application for the catalyst tablets produced according to the present invention is hydrogenation in a fixed bed. However, use in a fixed-bed reaction with upward and downward swirling motion of the catalyst material is likewise possible. The hydrogenation can be carried out in the gas phase or in the liquid phase. The hydrogenation is preferably carried out in the liquid phase, for example in the downflow or upflow mode.

In the downflow mode, the liquid feed comprising the carbonyl compound to be hydrogenated is allowed to trickle over the catalyst bed in the reactor which is under hydrogen pressure, so that a thin liquid film is formed on the catalyst. In contrast, when the upflow mode is employed, hydrogen gas is introduced into the reactor which is flooded with the liquid reaction mixture, so that the hydrogen ascends as gas bubbles through the catalyst bed.

In one embodiment, the solution to be hydrogenated is pumped in a single pass through the catalyst bed. In another embodiment of the process of the present invention, part of the product which has passed through the reactor is continuously taken off as product stream and optionally passed through a second reactor as defined above. The other part of the product is fed back into the reactor together with fresh feed comprising the carbonyl compound. This mode of operation will hereinafter be referred to as the circulation mode.

If the downflow mode is chosen as embodiment of the process of the present invention, preference is given to the circulation mode. More preferably, the process is carried out in the circulation mode using a main reactor and an after-reactor.

The process of the present invention is suitable for hydrogenating carbonyl compounds such as aldehydes and ketones to form the corresponding alcohols, with preference being given to aliphatic and cycloaliphatic saturated and unsaturated carbonyl compounds. In the case of aromatic carbonyl compounds, formation of undesirable by-products can occur as a result of hydrogenation of the aromatic ring. The carbonyl compounds may bear further functional groups such as hydroxy or amino groups. Unsaturated carbonyl compounds are generally hydrogenated to the corresponding saturated alcohols. The term "carbonyl compounds" as used for the purposes of the invention encompasses all compounds which contain a C=O group, including carboxylic acids and their derivatives. It is of course also possible to hydrogenate two or more carbonyl compounds together. Furthermore, the individual carbonyl compound to be hydrogenated may contain more than one carbonyl group.

The process of the present invention is preferably employed for the hydrogenation of aliphatic aldehydes, hydroxy aldehydes, ketones, acids, esters, anhydrides, lactones and sugars.

Preferred aliphatic aldehydes are branched and unbranched saturated and/or unsaturated aliphatic $C_2$–$C_{30}$-aldehydes, as are obtainable, for example, from linear or branched olefins having an internal or terminal double bond by means of the oxo process. Oligomeric compounds which may contain more than 30 carbonyl groups can also be hydrogenated.

Examples of aliphatic aldehydes are:

formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, glutaraldehyde.

Apart from the short-chain aldehydes mentioned, it is also possible to use, in particular, long-chain aliphatic aldehydes as can be obtained, for example, from linear α-olefins by means of the oxo process.

Particular preference is given to enalization products such as 2-ethylhexenal, 2-methylpentenal, 2,4-diethyloctenal or 2,4-dimethylheptenal.

Preferred hydroxyaldehydes are $C_3$–$C_{12}$-hydroxyaldehydes as are obtainable, for example, from aliphatic and cycloaliphatic aldehydes and ketones by aldol reaction with themselves or formaldehyde. Examples are 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, hydroxypivalaldehyde. Particular preference is given to hydroxypivalaldehyde (HPA) and dimethylolbutanal (DMB).

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, 2,3-butanedione, 2,4-pentanedione, 2,5-hexanedione and methyl vinyl ketone.

Furthermore, carboxylic acids and derivatives thereof, preferably ones having 1–20 carbon atoms, can also be reacted. Particular mention may be made of the following:

carboxylic acids such as formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexanecarboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic acid halides such as the chlorides or bromides of the abovementioned carboxylic acids, in particular acetyl chloride or bromide, stearoyl chloride or bromide and benzoyl chloride or bromide, which are, in particular, dehalogenated;

carboxylic esters such as the $C_1$–$C_{10}$-alkyl esters of the abovementioned carboxylic acids, in particular methyl formate, ethyl acetate, butyl butyrate, dimethyl terephthalate, dimethyl adipate, dimethyl maleate, methyl (meth)acrylate, butyrolactone, caprolactone and polycarboxylic esters such as polyacrylic and polymethacrylic esters and their copolymers and polyesters such as polymethyl methacrylate, terephthalic esters and other industrial polymers; in these cases, in particular, hydrogenolyses, i.e. the conversion of esters into the corresponding acids and alcohols, are carried out;

fats;

carboxylic anhydrides such as the anhydrides of the abovementioned carboxylic acids, in particular acetic anhydride, propionic anhydride, benzoic anhydride and maleic anhydride;

carboxylic amides such as formamide, acetamide, propionamide, stearamide and terephthalamide.

Furthermore, hydroxycarboxylic acids, e.g. lactic, malic, tartaric or citric acid, or amino acids, e.g. glycine, alanine, proline and arginine, and peptides can also be reacted.

The process of the present invention is particularly preferably used for hydrogenating aldehydes and hydroxyaldehydes.

The carbonyl compound to be hydrogenated can be fed to the hydrogenation reactor either alone or as a mixture with the product of the hydrogenation reaction. The carbonyl compound can be used in undiluted form or an additional solvent can be employed. Suitable additional solvents are, in particular, water and alcohols such as methanol, ethanol and the alcohol which is formed under the reaction conditions. Preferred solvents are water, THF, NMP and ethers such as dimethyl ether, diethyl ether and MTBE; particular preference is given to water.

The hydrogenation both in the upflow mode and in the downflow mode, in each case preferably using the circulation mode, is generally carried out at from 50 to 250° C., preferably from 70 to 200° C., particularly preferably from 100 to 140° C., and a pressure of from 15 to 250 bar, preferably from 20 to 200 bar, particularly preferably from 25 to 100 bar.

High conversions and selectivities are achieved in the process of the present invention and the catalysts display a high chemical stability in the presence of the reaction mixture. For the same support material, the catalysts produced according to the present invention are, compared to catalysts which have been produced according to the prior art, both easier to shape into tablets and, after heat treatment of the shaped tablets, have a significantly greater mechanical strength both in the oxidic state and in the reduced state, as a result of which the process of the present invention is particularly economical.

The invention is illustrated by the following examples.

EXAMPLES

Catalyst Production

All percentages reported under this subheading are by weight unless indicated otherwise. The stated percentage compositions are based on the oxidic constituents of the finished catalysts.

Catalyst A (Comparison)

Catalyst A was produced by precipitation of a solution of copper nitrate with sodium carbonate solution. As substrate, use was made of a suspension of $TiO_2$ in water. The precipitated material formed in the precipitation was filtered off, washed and dried at 120° C. The dried powder was calcined at 200° C. for two hours and then mixed with 3% by weight of graphite and 20% by weight of metallic copper powder and pressed to form tablets having a diameter of 3 mm and a height of 3 mm. These tablets were calcined at 450° C. for 2 hours. The finished catalyst comprised 60% of CuO and 40% of $TiO_2$ and had a tapped density of 1498 g/l, a pore volume determined by Hg porosimetry of 0.21 ml/g, a BET surface area of 23.6 $m^2$/g, a copper surface area of 1.7 $m^2$/g and a lateral compressive strength of 54.5 N.

Catalyst B

The catalyst B according to the present invention was produced in the same way as catalyst A, except that it was pressed to form tablets having a diameter of 1.5 mm and a height of 1.5 mm. The finished catalyst comprised 60% of CuO and 40% of $TiO_2$ and had a tapped density of 1529 g/l, a pore volume determined by Hg porosimetry of 0.21 ml/g, a BET surface area of 26.8 $m^2$/g, a copper surface area of 1.8 $m^2$/g and a lateral compressive strength of 32.1 N.

Example 1

Hydrogenation of Dimethylolbutanal (DMB) to Trimethylolpropane (TMP) in the Downflow Mode with Recirculation and an After-Reactor The starting solution employed was a mixture of 30% of DMB and 70% of water. This mixture was hydrogenated by means of the catalysts A and B in a reactor having a volume of 210 ml (130 ml main reactor and 80 ml after-reactor) in the circulation mode at a throughput of 7.5 l/h and temperatures of 120° C. (main reactor) and 130° C. (after-reactor) and a pressure of 90 bar, with the WHSV over the catalyst being from 0.2 $kg_{DMB}/(1_{cat} \cdot h)$ and 2 $kg_{DMB}/(1_{cat} \cdot h)$.

Table 1 shows a comparison of the catalyst B according to the present invention with the catalyst A which is not according to the present invention and illustrates the high conversions and selectivities of B.

TABLE 1

Results from example 1 (downflow mode with recirculation and after-reactor)

| | WHSV [kg/l*h] | Catalyst A | Catalyst B |
|---|---|---|---|
| Conversion/% (from GC % by area) | 0.2 | 99.6 | 99.9 |
| | 0.7 | 97.9 | 99.7 |
| | 1.2 | 96.4 | 99.1 |
| | 2.0 | 89.2 | 92.8 |
| Selectivity/% (from GC % by area) | 0.2 | 92.6 | 93.8 |
| | 0.7 | 92.4 | 93.7 |
| | 1.2 | 91.1 | 93.4 |
| | 2.0 | 88.5 | 90.2 |

We claim:

1. A process for the catalytic hydrogenation of an aliphatic hydroxyaldehyde or a mixture of two or more of these aldehydes in the presence of catalyst tablets which comprise an inorganic, $TiO_2$-containing support and, as active component, copper or a mixture of copper with at least one metal selected from the group consisting of zinc, aluminum, cerium, nobel metals and metals of transition group VIII and whose copper surface area is not more than 10 $m^2$/g, metallic copper powder being added to the catalyst material prior to tabletting, wherein the diameter d and/or the height h of the tablets is in each case 1.5 mm.

2. A process as claimed in claim 1, wherein the support material comprises a mixture of $TiO_2$ and $Al_2O_3$ or a mixture of $TiO_2$ and $ZrO_2$ or a mixture of $TiO_2$ and $Al_2O_3$ and $ZrO_2$.

3. A process as claimed in claim 1, wherein the diameter and height of the catalyst tablets are equal.

4. A catalyst tablet which comprises an inorganic, $TiO_2$-containing support and, as active component, copper or a mixture of copper with at least one metal selected from the group consisting of zinc, aluminum, cerium, nobel metals and metals of transition group VIII and whose copper surface area is not more than 10 $m^2$/g, metallic copper powder being added to the catalyst material prior to tabletting, wherein the diameter d and/or the height h of the tablet is in each case 1.5 mm.

5. A catalyst tablet as claimed in claim 4, wherein the diameter and height of the tablet are equal.

* * * * *